United States Patent
Sarnowski et al.

(10) Patent No.: US 6,287,338 B1
(45) Date of Patent: Sep. 11, 2001

(54) PRE-STRESSING DEVICES INCORPORATING MATERIALS SUBJECT TO STRESS SOFTENING

(75) Inventors: Edward J. Sarnowski; Riyad E. Moe, both of Austin; Donald W. James, Elgin, all of TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/265,791

(22) Filed: Mar. 10, 1999

(51) Int. Cl.[7] .............................. A61F 2/24; A61B 19/00
(52) U.S. Cl. .............................. 623/2.1; 128/898
(58) Field of Search .................. 623/1.26, 2.1, 623/2.12, 2.13, 2.15, 2.18, 2.19; 128/898, 842; 8/94.11; 524/525

(56) References Cited

U.S. PATENT DOCUMENTS

| | | | |
|---|---|---|---|
| 3,966,401 | * | 6/1976 | Hancock et al. .................. 8/94.11 |
| 4,362,840 | * | 12/1982 | Tabar et al. ...................... 524/525 |
| 4,372,743 | * | 2/1983 | Lane ................................. 8/94.11 |
| 4,419,480 | * | 12/1983 | Tabar et al. ...................... 524/525 |
| 4,473,423 | * | 9/1984 | Kolff ................................. 156/245 |
| 4,800,603 | * | 1/1989 | Jaffe ................................. 8/94.11 |
| 5,279,612 | * | 1/1994 | Eberhardt ........................ 8/94.11 |
| 5,376,110 | * | 12/1994 | Tu et al. .......................... 623/1 |
| 5,526,823 | * | 6/1996 | Wheeler et al. ................. 128/842 |
| 5,769,780 | * | 6/1998 | Hata et al. ....................... 600/36 |
| 6,117,169 | * | 9/2000 | Moe .................................. 623/2.12 |

FOREIGN PATENT DOCUMENTS

| | | | |
|---|---|---|---|
| 8400066 | 1/1985 | (NL) | ....... 623/2 |
| WO 9843557 | 8/1998 | (WO) | ....... 623/2 |

OTHER PUBLICATIONS

Sing, H.W., et al., "In Vitro Pulsatile Flow Evaluation of a Stentless Procines Aortic Bioprosthesis", ASAIO Journal, vol. 41, No. 1, Jan. 1, 1995, pp. 89–94.

Gloeckner, D.C., et al., "Effects of Mechanical Fatigue on the Bending Properties of the Porcine Bioprosthetic Heart Valve", ASAIO Journal, vol. 45, No. 1, 01/99, pp. 59–63.

* cited by examiner

Primary Examiner—Corrine McDermott
Assistant Examiner—Alvin Stewart
(74) Attorney, Agent, or Firm—Blossom E. Loo (57) ABSTRACT

A method and apparatus for pre-stressing devices incorporating materials subject to stress softening is disclosed, as well as the resulting device. The method includes fabricating a heart valve with an inflow side and an outflow side. At least a portion of the heart valve includes a material subject to stress softening. The material experiences stress when a pressure differential occurs between the inflow side and the outflow side of the valve. The method includes creating a stress in the material prior to implantation in order to stabilize the stress/strain response of the material prior to implantation.

26 Claims, 10 Drawing Sheets

PRE-STRESSING DEVICES INCORPORATING MATERIALS SUBJECT TO STRESS SOFTENING

FIELD OF THE INVENTION

The present invention relates to pre-stressing, prior to use, devices incorporating materials subject to stress softening. In particular, the present invention relates to pre-stressing elastomer objects subject to stress softening. Even more particularly, the present invention relates to pre-stressing prosthetic heart valves made, at least partially, of an elastomer.

BACKGROUND OF THE INVENTION

Some materials (for example nylon, certain wool fibers, and elastomers) experience a phenomenon called "stress softening." As a result of this phenomenon, the stress-strain curve of a material prior to being loaded is different from that of the material after being loaded and unloaded. For some materials, the properties of the first loading and any subsequent loading can be dramatically different. Elastomers are subject to stress softening in a behavior known as the "Mullins' Effect."

Many devices include materials subject to stress softening. For example, prosthetic heart valves sometimes include materials subject to stress softening, including elastomers.

Ever since 1950, when blood oxygenators made open heart surgery feasible, it has been possible to treat some forms of heart disease by replacing one of the patient's heart valves with a prosthetic valve. Early heart valve prostheses included ball-and-cage valves and disc-and-cage valves in which a ball or a disc was housed in a cage. One side of the cage provided an orifice through which blood flowed either into or out of the heart, depending on the valve being replaced. When blood flowed in a forward direction, the energy of the blood flow forced the ball or disc to the back of the cage allowing blood to flow through the valve. When blood attempted to flow in a reverse direction, or "regurgitate", the energy of the blood flow forced the ball or disc into the orifice in the valve and blocked the flow of blood.

A bi-leaflet valve comprised an annular valve body in which two opposed leaflet occluders were pivotally mounted. The occluders were substantially rigid and moved between a closed position, in which the two leaflets were mated and blocked blood flow in the reverse direction, and an open position, in which the occluders were pivoted away from each other and did not block blood flow in the forward direction. The energy of blood flow caused the occluders to move between their open and closed positions.

A tri-leaflet valve comprised an annular valve body in which three leaflets were mounted to a portion of the valve body, called a "stent," located at the circumference of the annulus. When blood flowed in the forward direction, the energy of the blood flow deflected the three leaflets away from the center of the annulus and allowed blood to flow through. When blood flowed in the reverse direction, the three leaflets engaged each other in a coaptive region, occluded the valve body annulus and prevented the flow of blood. The valve leaflets were made from tissue, such as specially treated porcine or bovine pericardial tissue, or from man-made materials such as ceramic materials, elastomers or other biocompatible polymers.

SUMMARY OF THE INVENTION

The present invention is directed toward pre-stressing elastomer devices that can be stress softened. The design of the device utilizing the present invention uses properties of the materials after stress softening rather than before. Prior to implantation, the device is pre-stressed to subject it to the stress that it is expected to experience in use. Pre-stressing causes the device to experience stress softening and operate as designed.

In general, in one aspect, the invention features a method for manufacturing a prosthetic heart valve. The method comprises fabricating a heart valve. The valve has an inflow side and an outflow side. At least a portion of the heart valve comprises a material subject to stress softening. The material experiences stress when a pressure differential occurs between the inflow side and the outflow side. The method includes creating a stress in the material prior to use.

Implementations of the invention may include one or more of the following: Creating a pressure differential may comprise raising the stress to the point where the material subject to stress softening experiences the stress that it is expected to experience in use.

Creating a pressure differential may comprise raising the stress to the point where the material subject to stress softening experiences more stress than it is expected to experience in use. The method may comprise removing the stress. The method may comprise cyclically creating and removing the stress a predefined number of times. Creating the stress may comprise applying pressure to the outflow side of the valve with a fluid. The fluid may be a gas or a liquid. Creating the stress may comprise applying a weight to the valve. Applying a weight may comprise applying a weight to the outflow side of the valve or applying a weight to the inflow side of the valve. Creating the stress may comprise applying a vacuum to the valve, accelerating the valve, vibrating the valve, applying a static head of fluid to the outflow side of the valve, pumping fluid into a chamber on the outflow side of the valve, pumping fluid out of a chamber on the inflow side of the valve, or creating a pressure differential between the inflow side and the outflow side of the valve. The valve may have an annular portion supporting three leaflets and the method may further comprise supporting the annular portion of the valve when creating the stress. Supporting the annular portion of the valve may comprise placing an annular collar inside the annular portion of the valve.

In general, in another aspect, the invention features a method for manufacturing an object. At least a portion of the object comprises materials subject to stress softening. The method comprises pre-stressing prior to use the portion of the object comprising materials subject to stress softening.

In general, in another aspect the invention features an object comprising a flexible member. The flexible member comprises a material subject to stress softening. The flexible member is pre-stressed to the stress it is expected to experience in use.

Implementations of the invention may include one or more of the following. The material may comprise an elastomer. The object may comprise a valve. The valve may comprise a valve body and three flexible leaflets coupled to the valve body. The flexible member may be part of the valve. The flexible member may have a different performance after being pre-stressed than before being pre-stressed. The performance of the flexible member after pre-stressing may be closer to a desired performance of the flexible member than the performance of the flexible member before pre-stressing.

In general, in another aspect, the invention features a tri-leaflet heart valve comprising an elastomer portion. The elastomer portion is pre-stressed, prior to implantation, to the stress it is expected to experience in use.

Implementations of the invention may include one or more of the following. The elastomer portion may be pre-stressed, prior to implantation, beyond the stress it is expected to experience in use. The tri-leaflet heart valve may comprise an annular valve body and three leaflets coupled to the annular valve body. The annular valve body may comprise the pre-stressed elastomer portion. At least one of the three leaflets may comprise the pre-stressed elastomer portion.

In general, in another aspect, the invention features a method for pre-stressing a tri-leaflet heart valve to meet a performance requirement. The heart valve has an inflow side and an outflow side and comprises an elastomer portion subject to stress softening. The elastomer portion of the heart valve experiences stress when a pressure differential occurs between the inflow side and the outflow side. The method includes creating a stress in the elastomer portion. The method includes repeating a predetermined number of cycles: raising the stress to a predetermined amount and lowering the stress to cause the heart valve to meet the performance requirement.

Implementations of the invention may include one or more of the following. The predetermined number of cycles may be less than 100. The predetermined number of cycles may be between 25 and 75.

DESCRIPTION OF THE PREFERRED EMBODIMENTS

Figure 1:
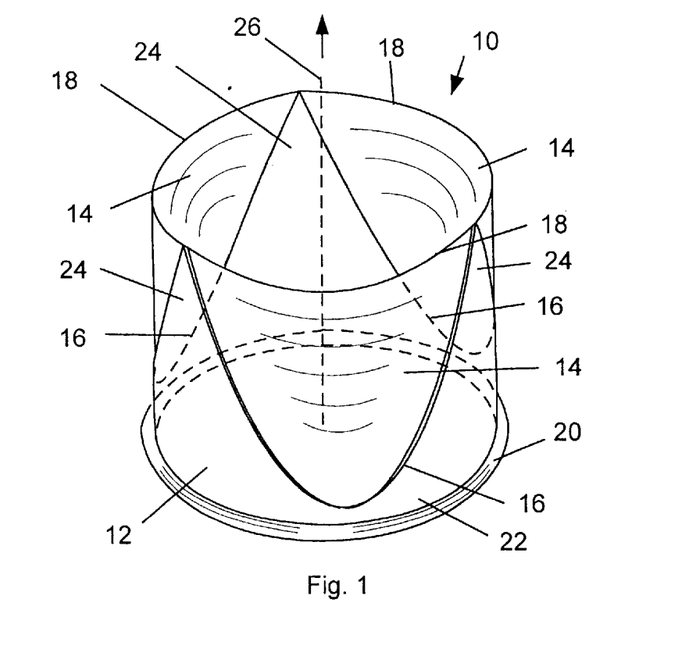
FIG. 1 is a perspective view of a polymer valve.

A tri-leaflet heart valve prosthesis 10 comprises an annular elastic valve body 12 and three flexible leaflets 14 made of a biocompatible polymer such as silicone or polyurethane, as shown in FIG. 1. Each leaflet has an attachment edge by which it is coupled to the valve body along an attachment curve 16. Each leaflet has a free edge 18 that is not coupled to the valve body. A sewing ring 20 is coupled to the base of the valve body 12 and provides a place for sutures to be applied when the valve is implanted. The valve body comprises an annular base 22 and a leaflet support, comprising three shaped posts 24, that supports the leaflets 14.

Figure 2:
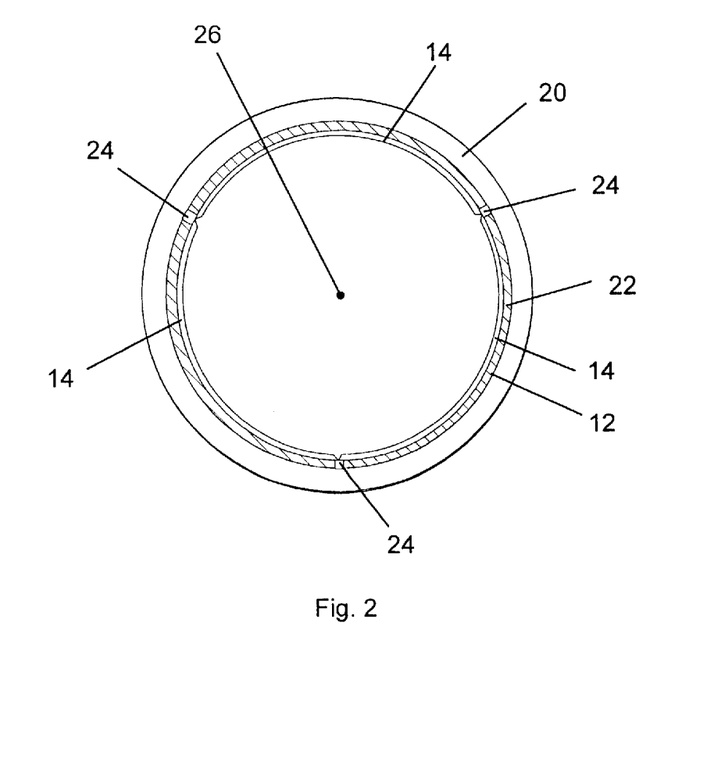
FIG. 2 is a top view of the polymer valve of FIG. 1.

When fluid flow is in the forward direction, i.e. in the direction of the arrow shown in FIG. 1, the pressure of the blood flow causes the leaflets 14 to deflect away from a central longitudinal axis 26 of the valve body that is generally parallel to the three posts 24. In this "open" position, the leaflets 14 define a large flow orifice, as shown in FIG. 2. With the leaflets in the open position shown in FIGS. 1 and 2, the valve presents little resistance to fluid flow.

Figure 3:
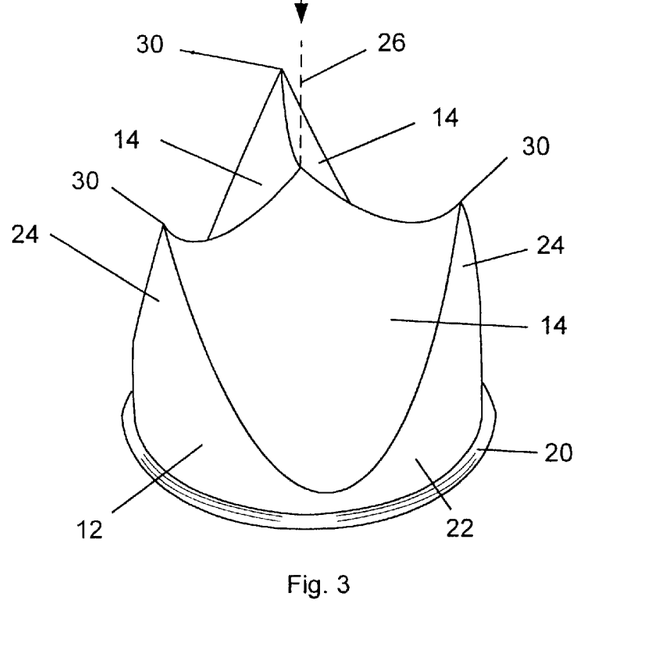
FIG. 3 is a perspective view of a polymer valve.
Figure 4:
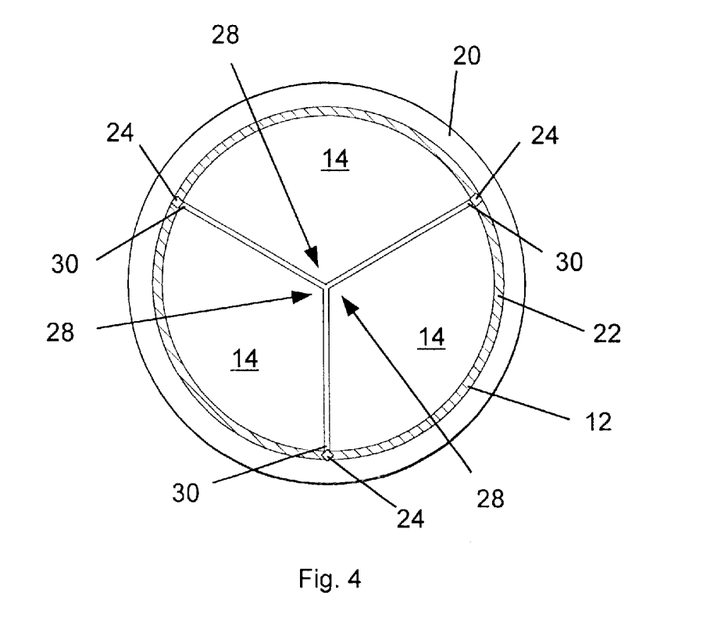
FIG. 4 is a top view of the polymer valve of FIG. 3.

When the pressure of blood flow is insufficient to overcome the elastic force biasing the valve toward a closed or partially closed position, the leaflets deflect toward axis 26, as shown in FIGS. 3 and 4. In this "closed" position, each leaflet would occlude more than one-third of the valve body's orifice were it not for the presence of the other leaflets. Consequently, when the three leaflets deflect toward axis 26, they engage each other and form coaptive areas along the free edges 18, which help the valve seal against reverse flow. Further, when the leaflets press together, each leaflet forms a "triple point" 28 at the point where the three leaflets come together, as shown in FIG. 4. The place where the leaflets 14 come together adjacent the posts 24 is called the "commissure" 30, as shown in FIG. 3.

From this discussion, it is clear that a tri-leaflet heart valve experiences mechanical stress during use. Each leaflet experiences one load when the valve opens to allow the leaflet to deflect out of the way of blood flow. When the blood flow stops, the leaflets are unloaded and return to the position shown in FIG. 3. Subsequently, when the blood attempts to flow in the opposite direction, or "regurgitate", the leaflets experience a different load causing the leaflets to bow toward axis 26 as shown in FIG. 3. When the blood pressure in the "regurgitation" direction ends, the leaflets are unloaded. The rest of the valve experiences similar mechanical stresses as the valve operates.

Furthermore, these stresses are applied to the valve cyclically. That is, because the prosthetic heart valve is replacing a native heart valve it will rhythmically and cyclically repeat the cycle of opening, closing and experiencing back pressure. This cycle of loading and unloading the valve will stress soften the portions of the valve subject to that phenomenon.

Figure 5:
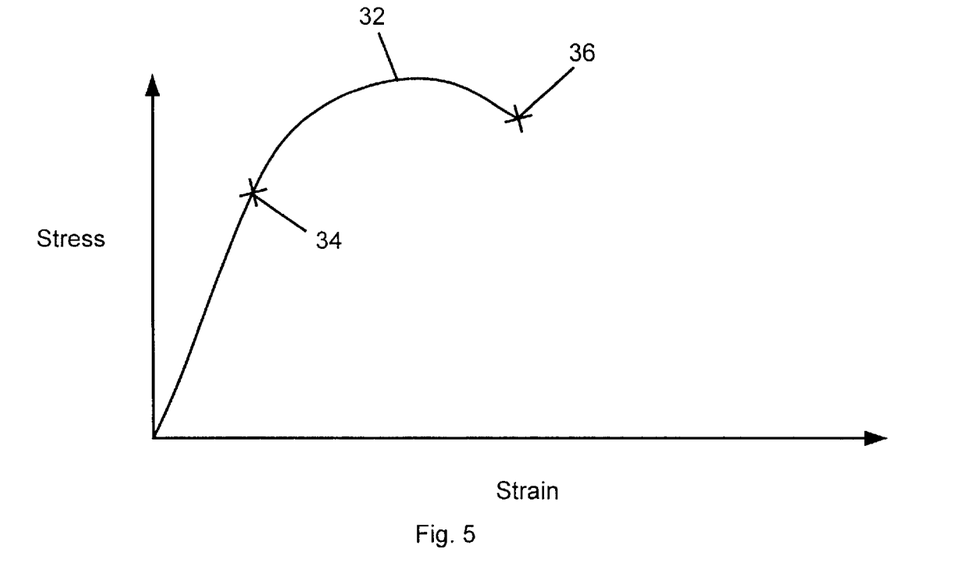
FIG. 5 is an example of a stress/strain plot for a metal.
Figure 6:
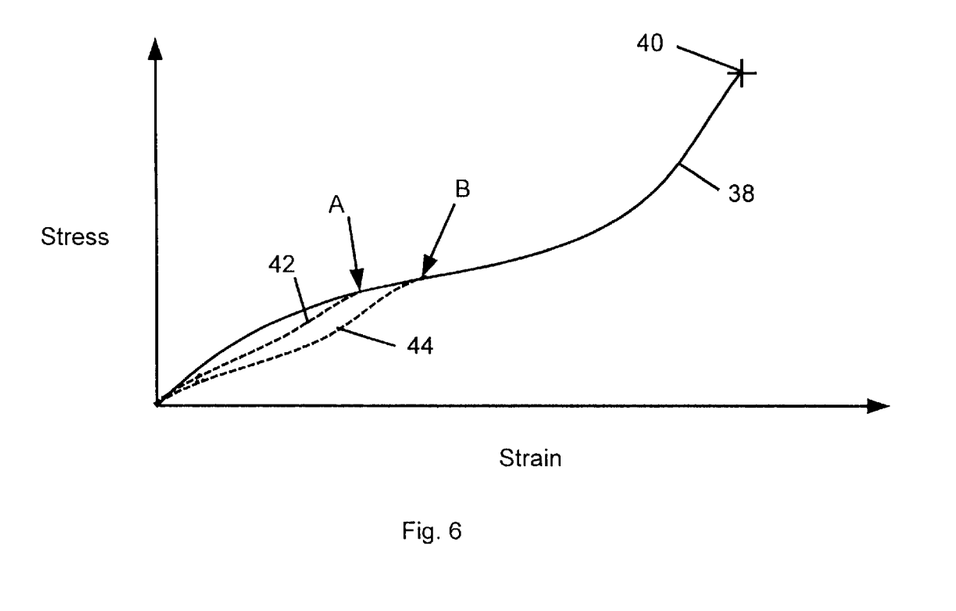
FIG. 6 is a stress/strain plot for an elastomer subject to stress softening.

Referring to FIGS. 5 and 6, the effect of this cycle of loading and unloading the valve is to change its mechanical characteristics and, consequently, to change the performance of the valve. FIG. 5 shows the stress-strain plot for a metal. A curve 32 shows the relationship between stress and strain for the metal. At a level of stress defined by the yield point 34, the material ceases to be elastic. Beyond the yield point 34, plastic deformation is induced. At a level of strain defined by a cross 36 the metal fails. Absent the effect of stress softening, the elastic loading curve is the same as the elastic unloading curve. That is, the relationship between stress and strain will be the same as the metal is being loaded as when it is being unloaded as long as the loading remains below the yield point 34. Further, the relationship between elastic stress and strain will remain the same from one loading to the next.

FIG. 6 shows the stress-strain plot for a material subject to stress softening, such as an elastomer. Again, a curve 38, known as the "virgin" stress/strain curve, shows the relationship between stress and strain for the material. This material does not exhibit an elastic and plastic region as discussed with respect to FIG. 5. At a level of strain defined by a cross 40, the material fails. The unloading curve may not be the same as the loading curve for materials subject to stress softening. For example, if the material is loaded to point A on curve 38, stress softening will change the characteristics of the material so that it will unload along curve 42. Subsequently, when the material is loaded again it will follow curve 42 until it merges with and follows curve 38 as shown in FIG. 6. If the material is later loaded to point B on curve 38, it will follow curve 44 as it is unloaded. Subsequently, when the material is loaded again it will follow curve 44 until it merges with and follows curve 38 as shown in FIG. 6. Stress softening can occur at any point along the stress/strain curve.

If after being stress softened the material is left unstressed for a period of time, the stress/strain curve of the material will migrate toward, without necessarily reaching, the original "virgin" stress/strain curve. Once stress is applied to the material again, however, it will soften again. For some materials, this re-softening will occur more easily than the original softening. Materials in heart valves may not experience this phenomenon because their operational stress is continuous.

Thus, material subject to stress softening has a form of "memory". Its performance depends on the stresses that it has been subjected to in the past. Further, its performance will change each time the level of stress applied to the material reaches a high point the material has never experienced before. In the prior art, designers of devices incorporating materials subject to stress softening used the virgin stress-strain curve of materials in their designs. In the invention, the device is designed using the expected post-stress-softening properties of the materials. Consequently, the device will meet its performance criteria after stress softening has occurred. Further, the device is pre-stressed after manufacture but before being placed into use so that when it is placed into use it has the desired performance characteristics and a stabilized stress/strain response that will not vary under operational stresses.

In one embodiment of the invention, a prosthetic tri-leaflet heart valve including at least a portion that is subject to stress softening is designed using the post-stress-softening properties of the material. The valve is manufactured and, prior to being implanted, is subjected to stress so that the valve material subject to stress softening experiences the stress that the material is expected to experience in use. In one embodiment, the material is an elastomer.

Valve designers consider the stress-strain relationships of the materials they are using in the valve design to meet a variety of performance characteristics. For example, the shape of the free edge 18 of each leaflet 14 when the leaflet is between its fully open position and its fully closed position is partially governed by the stress-strain relationship of the leaflet material. That shape affects the valve's flow characteristics which are important to the proper operation of the valve after being implanted.

Further, the shapes of the leaflets in their closed positions are affected by the stress/strain relationship for the leaflet material. If the design of the leaflets does not anticipate the effect of stress softening, the leaflets may sag excessively or prolapse after implantation.

Another valve performance characteristic affected by the stress-strain relationships of the materials used to manufacture the valve is the stress level in the materials. Not having knowledge of stress softening might result in inaccurate estimates of the stress levels and therefore inaccurate estimates of fatigue life.

In a preferred embodiment, after the valve is designed using the post-stress-softening characteristics of the valve materials, and after the valve is manufactured, the valve is subjected to stress so that the material subject to stress softening is subjected to the stress it is expected to experience in use. In another embodiment, the material is subjected to more stress than it is expected to experience in use. In still another embodiment, the valve is implanted in the patient without subjecting it to any stress. In that embodiment, the material subject to stress softening is stress softened by the opening and closing of the valve as it is used.

Figure 7:
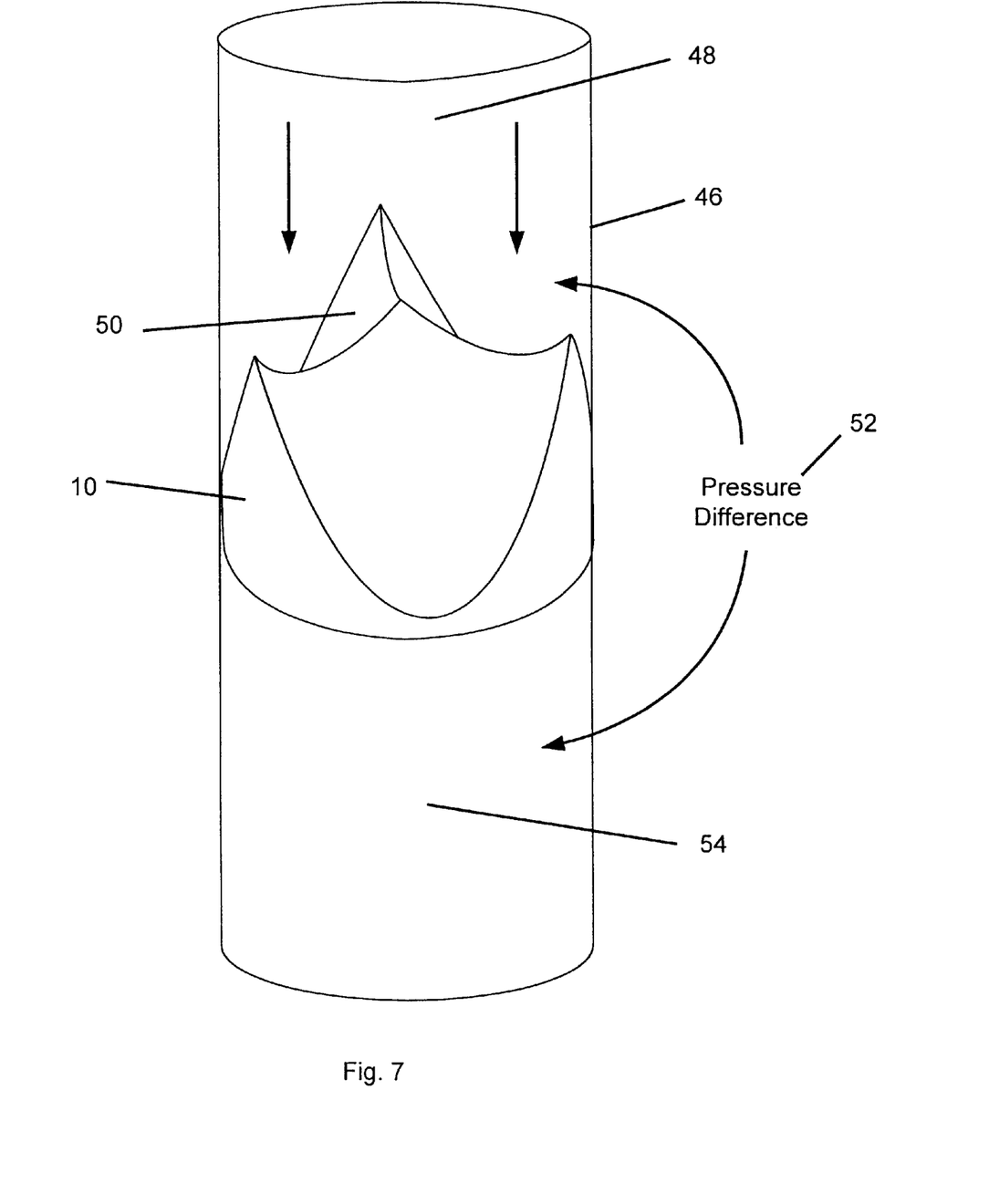
FIGS. 7, 8, 9, 10, 11, 12 and 13 illustrate apparatus for pre-stressing a tri-leaflet prosthetic heart valve.

FIG. 7 illustrates a generic apparatus 46 for pre-stressing the valve material subject to stress softening. The apparatus 46 allows stress to be placed on the valve material. For example, the apparatus may secure the valve 10. A fluid may be pumped into a chamber 48 on the outflow side 50 of the valve 10 to create a pressure difference 52 between the chamber 48 on the outflow side of the valve 10 and a chamber 54 on the inflow side of the chamber. The fluid may be a liquid, such as water, or a gas such as air.

Figure 8:
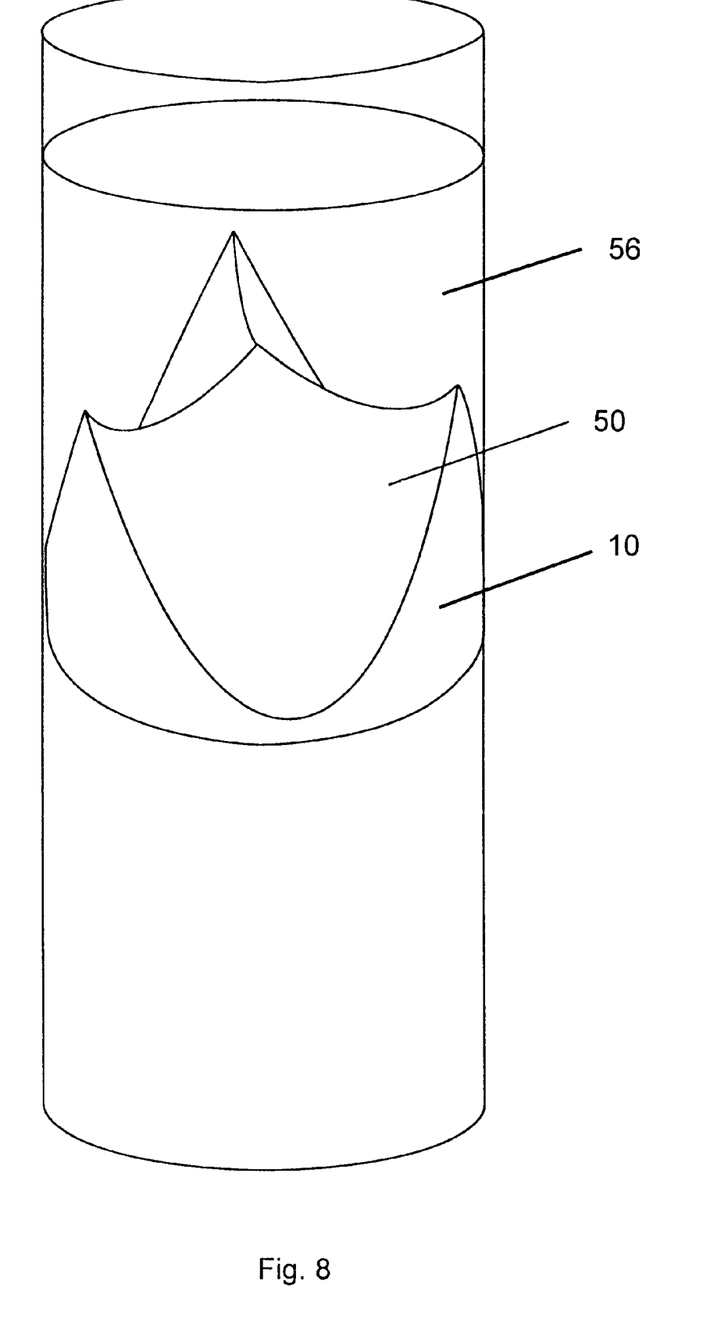

An example of the use of a liquid to create the stress is illustrated in FIG. 8. A column of water 56 on the outflow side 50 of the valve 10 places stress on the material of the valve 10.

Figure 9:
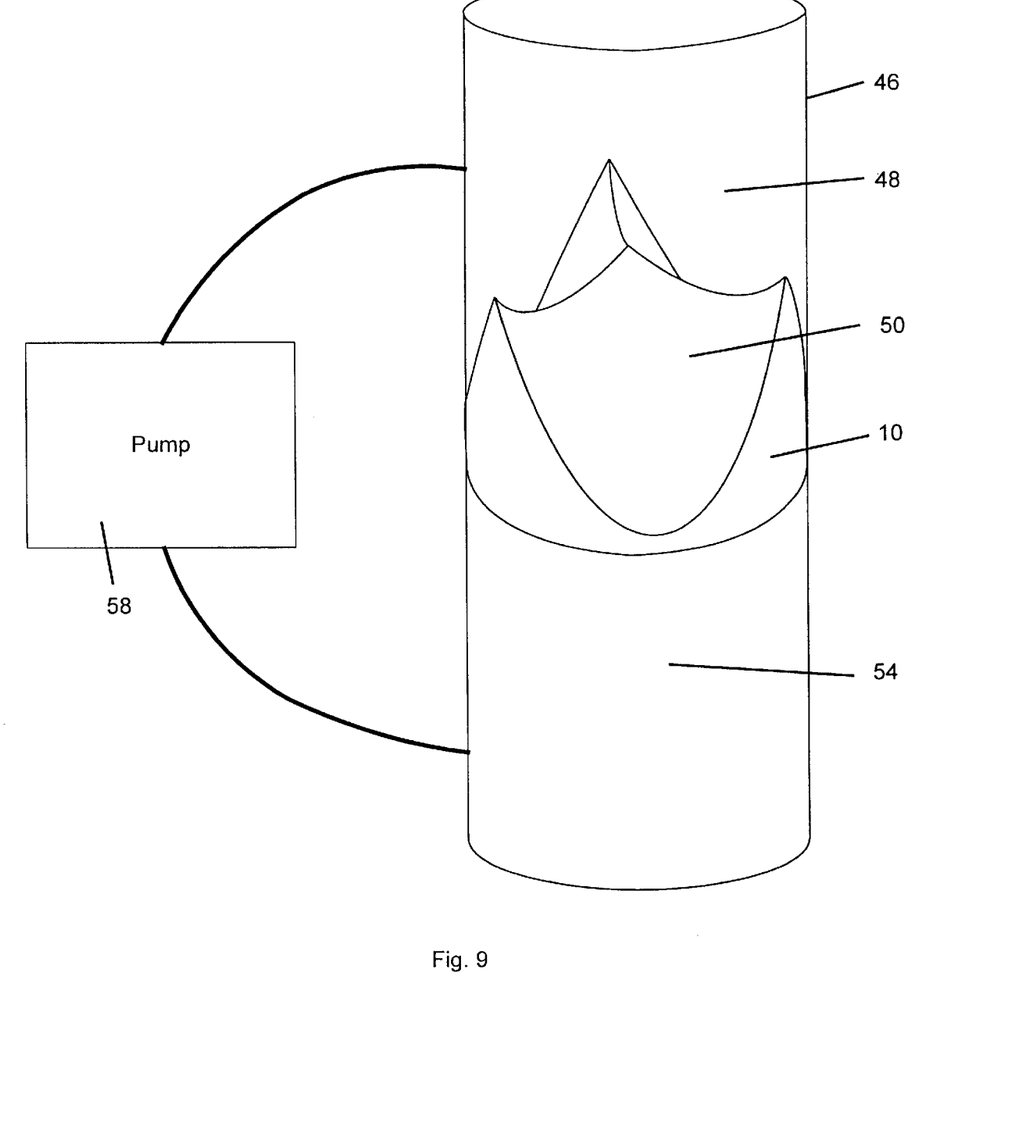

An example of the use of a gas to create the stress is illustrated in FIG. 9 (the apparatus shown in FIG. 9 could also be used with a liquid). A pump 58 pumps gas into the chamber 48 on the outflow side 50 of the valve and, optionally, evacuates gas from the chamber 54 on the inflow side of the valve. This action creates a pressure differential between the inflow side of the valve 10 and the outflow side of the valve 10, which creates stress in the valve materials.

Figure 10:
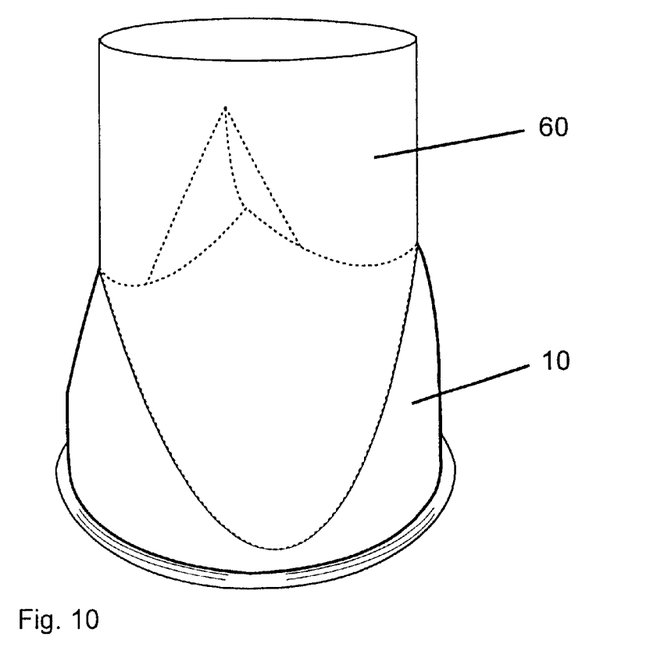

In another embodiment, the valve materials are subjected to stress by resting a solid mass 60, preferably sculpted to match the shape of the outflow side of the valve 10, on the outflow side of the valve, as shown in FIG. 10. The weight of the mass 60 pressing down on the outflow side of the valve 10 creates the desired stress.

Figure 11:
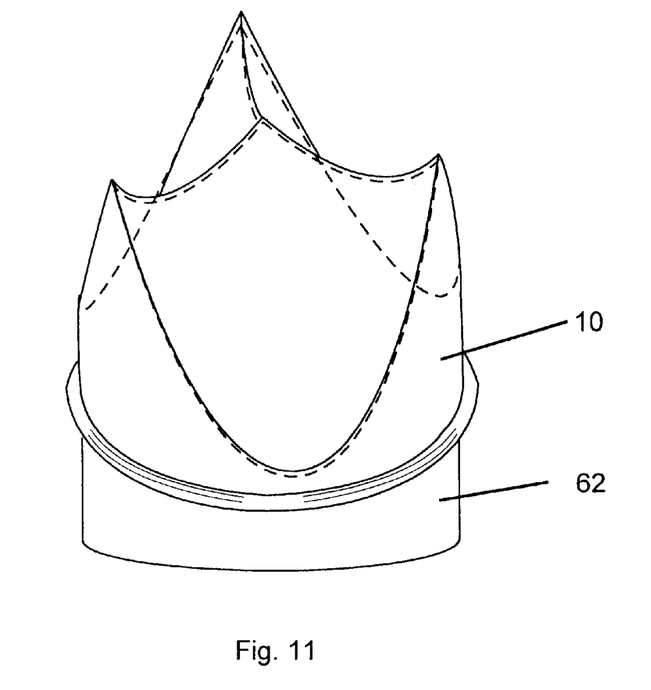

In another embodiment, a weight 62 is attached to the inflow side of the valve 10, preferably by an adhesive. The weight hanging from the inflow side of the valve creates the desired stress in the valve materials.

Figure 12:
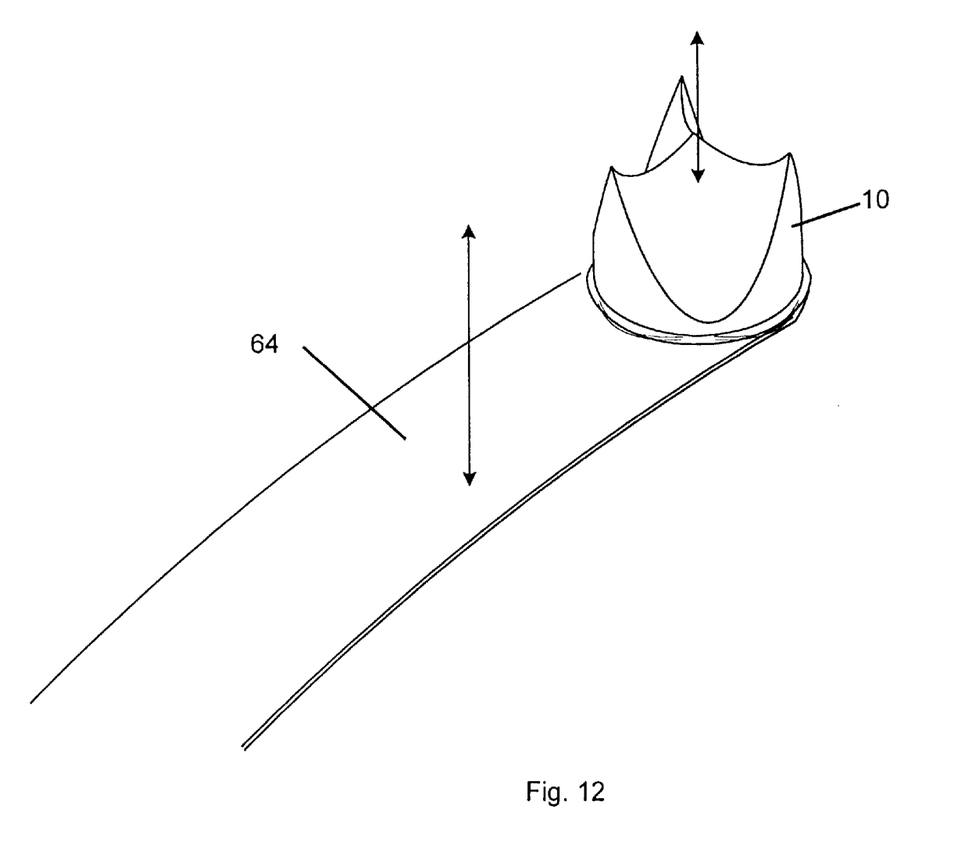

In another embodiment, the valve 10 is placed at the end of a flexible member 64, as illustrated in FIG. 12. A vibration is then initiated in the flexible member 64. The vibration of the flexible member 64 causes the valve to accelerate back and forth. The inertia of the valve gives rise to the desired stress.

Figure 13:
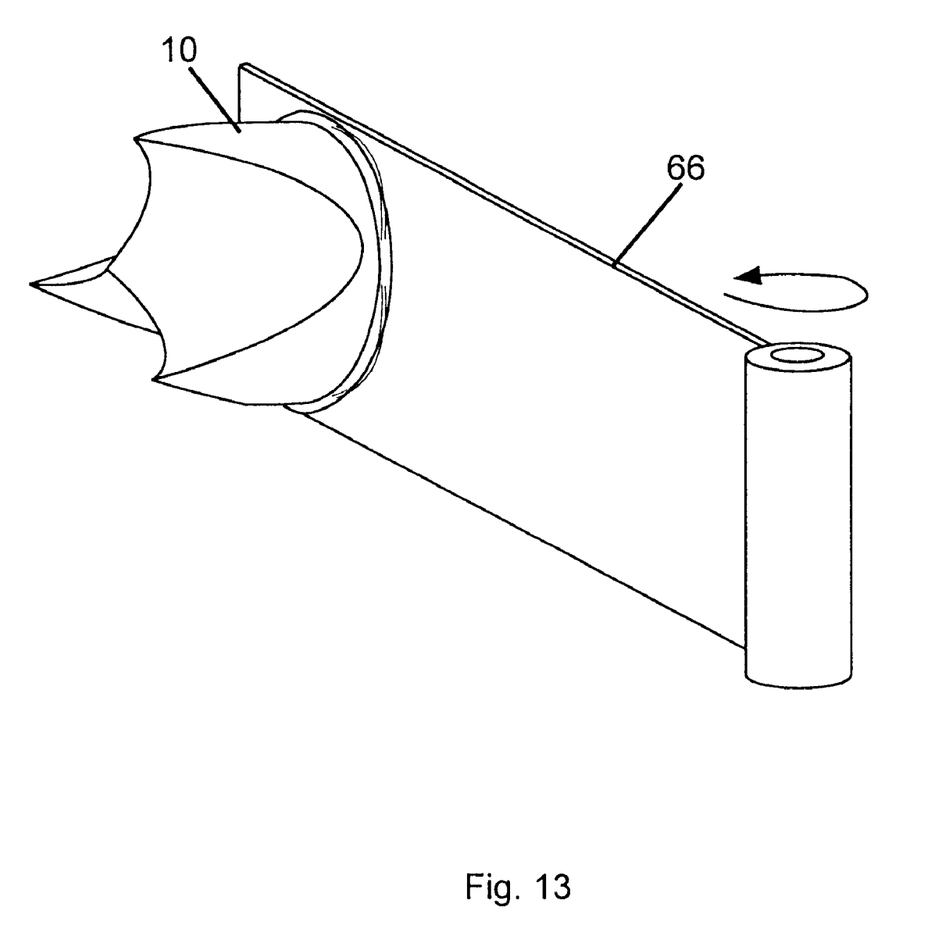

In another embodiment, the valve 10 is secured to a centrifuge 66, as shown in FIG. 13. The rotation of the centrifuge causes the materials of the valve 10 to experience the desired stress.

In some of the embodiments, the stress applied to accomplish pre-stressing is cyclically raised and lowered. That is, a cycle of raising the stress to a predetermined amount and then lowering it is repeated a predetermined number of times.

The predetermined amount of stress applied during each cycle depends on the design of the valve and the material or materials that are incorporated into the design. Further, the amount of stress applied and the rate that the stress is applied and lowered may vary from cycle to cycle.

Preferably, the number of cycles is between 1 and 100. More preferably, the number of cycles is between 25 and 75. Even more preferably, the number of cycles is between 30 and 50.

Figure 14:
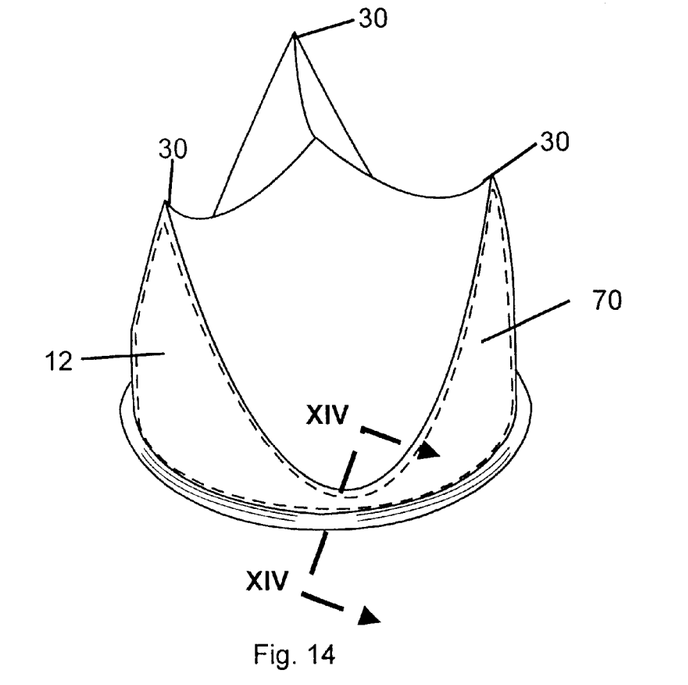
FIGS. 14 and 15 illustrate a device to prevent the inward deflection of a stent while a tri-leaflet prosthetic heart valve is being pre-stressed.
Figure 15:
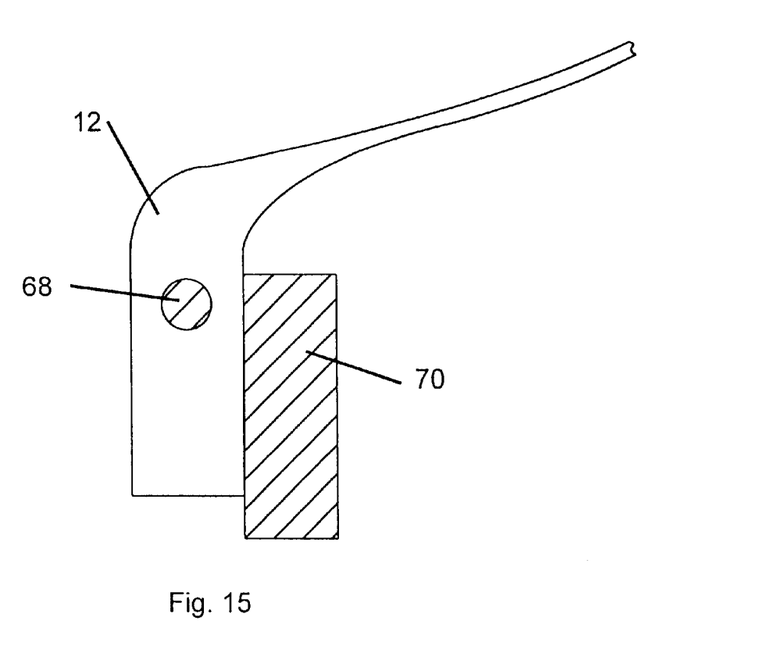

Pre-stressing the portions of the valve subject to stress softening beyond the level expected in use may stress and possibly damage portions of the valve that are not subject to stress softening. For example, a stent, which is a piece of metal or plastic configured to support the valve body that roughly has the shape of and follows the contours of the attachment curves 16, may yield under the stresses imposed by pre-stressing. To reduce the stress experienced by the stent 68, a hollow collar 70 is placed inside the valve body 12, as illustrated in FIGS. 14 and 15. The collar 70 reduces the inward deflection of the stent 68, particularly in the area of the commissures, as the valve is experiencing stress, such as, for example, when pressure is being applied to the outflow side of the valve.

The foregoing describes preferred embodiments of the invention and is given by way of example only. The invention is not limited to any of the specific features described herein, but includes all variations thereof within the scope of the appended claims.

What is claimed is:

1. A method for manufacturing a prosthetic heart valve, comprising the steps of:

fabricating a heart valve, the valve having an inflow side and an outflow side, at least a portion of the heart valve comprising an elastomer material subjected to stress softening, the material experiencing stress when a pressure differential occurs between the inflow side and the outflow side; and creating the stress in the material prior to use.

2. The method of claim 1 where creating a pressure differential comprises raising the stress to the point where the material subject to stress softening experiences the stress that it is expected to experience in use.

3. The method of claim 2, wherein creating a pressure differential comprises raising the stress to the point where the material subject to stress softening experiences more stress that it is expected to experience in use.

4. The method of claim 1 further comprising removing the stress.

5. The method of claim 4 further comprising cyclically creating and removing the stress a predefined number of times.

6. The method of claim 1 wherein creating the stress comprises applying pressure to the outflow side of the valve with a fluid.

7. The method of claim 6 wherein the fluid is a gas.

8. The method of claim 6 wherein the fluid is a liquid.

9. The method of claim 1 wherein creating the stress comprises applying a weight to the valve.

10. The method of claim 9 wherein applying a weight comprises applying a weight to the outflow side of the valve.

11. The method of claim 9 wherein applying a weight comprises applying a weight to the inflow side of the valve.

12. The method of claim 1 wherein creating the stress comprises applying a vacuum to the valve.

13. The method of claim 1 wherein creating the stress comprises accelerating the valve.

14. The method of claim 1 wherein creating the stress comprises vibrating the valve.

15. The method of claim 1 wherein creating the stress comprises applying a static head of fluid to the outflow side of the valve.

16. The method of claim 1 wherein creating the stress comprises pumping fluid into a chamber on the outflow side of the valve.

17. The method of claim 1 wherein creating the stress comprises pumping fluid out of the chamber on the inflow side of the valve.

18. The method of claim 1 wherein creating the stress comprises creating a pressure differential between the inflow side and the outflow side of the valve.

19. The method of claim 1 wherein the valve has an annular portion supporting three leaflets, further comprising supporting the annular portion of the valve when creating the stress.

20. The method of claim 19 wherein supporting the annular portion of the valve comprises placing an annular collar inside the annular portion of the valve.

21. A method for manufacturing, a heart valve, the heart valve having at least a portion that includes an elastomer material subject to stress softening comprising the steps of: pre-stressing the elastomer material subject to stress softening prior to use.

22. The method of claim 21, wherein pre-stressing comprises subjecting the portion of the object comprising the material subject to stress softening to the stress it is expected to experience in use.

23. The method of claim 21, wherein pre-stressing comprises subjecting the material to more stress than the material is expected to experience in use.

24. A method for pre-stressing a tri-leaflet heart valve to meet a performance requirement, the method comprising the steps of:

providing the heart valve having an inflow side and an outflow side, the heart valve comprising an elastomer portion subject to stress softening;

creating a stress in the elastomer portion by providing a pressure differential between the inflow side and the outflow side;

repeating a predetermined number of cycles;

raising the stress to a predetermined amount; and lowering the stress to cause the heart valve to meet the performance requirement.

25. The method of claim 24 wherein the predetermined number of cycles is less than 100.

26. The method of claim 24 wherein the predetermined number of cycles is between 25 and 75.

* * * * *